United States Patent [19]

Gowing

[11] Patent Number: 4,635,487
[45] Date of Patent: Jan. 13, 1987

[54] FLUID SAMPLER

[75] Inventor: Scott Gowing, Rockville, Md.

[73] Assignee: The United States of America as represented by the United States Department of Navy, Washington, D.C.

[21] Appl. No.: 792,374

[22] Filed: Oct. 29, 1985

[51] Int. Cl.⁴ .............................................. G01N 1/10
[52] U.S. Cl. ............................. 73/864.62; 73/864.63
[58] Field of Search ................ 73/863.02, 863.03, 864, 73/864.31, 864.34, 864.35, 864.51, 864.52, 864.61, 864.62, 864.63, 864.64, 864.67, 864.91

[56] References Cited

U.S. PATENT DOCUMENTS

| | | | |
|---|---|---|---|
| 2,699,680 | 1/1955 | Ferguson | 73/864.61 |
| 3,277,723 | 10/1966 | Bodman et al. | 73/864.62 |
| 3,866,474 | 2/1975 | Hasselmann | 73/864.34 |
| 3,892,130 | 7/1975 | Winget et al. | 73/864.62 |
| 3,950,999 | 4/1976 | Edwards | 73/864.62 |
| 4,008,621 | 2/1977 | Ostojic et al. | 73/864.52 |

Primary Examiner—Stewart J. Levy
Assistant Examiner—Robert R. Raevis
Attorney, Agent, or Firm—Luther A. Marsh

[57] ABSTRACT

A rubber bladder enclosed in a pressure tank having a valved opening is inflated by bladder inflation means to a pressure corresponding to the hydrostatic or other pressure of the environment to be sampled. Once the apparatus is located in the environment which is to be sampled, means for slowly exhausting the gas from the bladder, possibly a pump, are activated whereby hydrostatic or other pressure collapses the bladder and a fluid sample quiescently fills the pressure tank through the valved opening. When sample collection is complete, the valved opening, which is locally or remotely controllable, is closed and the sample is retrieved. Residual or ullage gas in the bladder maintains the sample at the pressure at which it was collected. Bladder inflating means are again employed after apparatus retrieval to initiate sample flow from the tank to an examining device or instrument at the same pressure that exists in the sampler.

2 Claims, 1 Drawing Figure

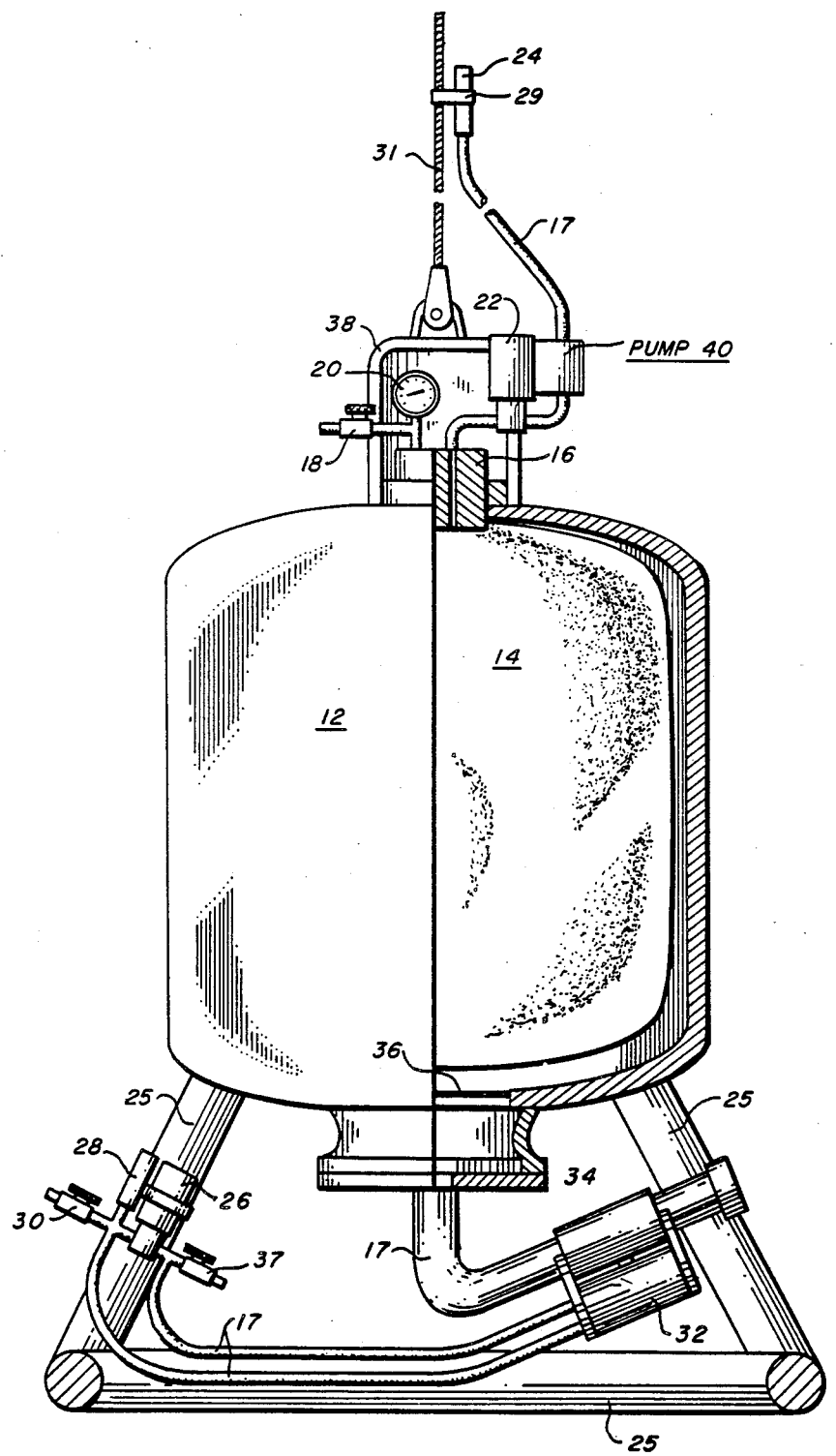

FLUID SAMPLER

BACKGROUND OF THE INVENTION

1. Field of the Invention

The present invention relates generally to samplers and, more particularly, to a receptacle type capture device especially suitable for collecting seawater samples for research purposes.

2. Description of the Prior Art

Bacteria, fungi, and microorganisms living in seawater are responsible for the degradation of organic material. Microbubbles in the same environment are known to provide nuclei for cavitation and to affect the mass transfer and the acoustic properties of the water. Investigation of microbiological and microbubble activity in the ocean, therefore, has come to be of considerable interest. In many cases, because of factors such as substantial depth of the environments of interest, investigation of biologicals and bubbles is possible only by quiescently recovering them in undamaged, unaltered form and by studying them as they exist in their usual ambient conditions of pressure, temperature, and chemistry. It is also often desirable to obtain undamaged, unaltered samples of other fluids such as lake water, gases, or contaminated air, and keep them during retrieval and examination at their usual ambient conditions.

In the past, a number of devices for collecting fluid samples have been employed. Most of these devices do not maintain pressure on the samples from their recovery to their examination; hence, samples become depressurized during retrieval or transfer. Those methods and devices which do maintain the samples at pressure have other shortcomings such as possessing a a variable or uncontrolled filling rate, requiring collector sizes much larger than the volume of sample collected, or lacking means for remote operations. Such shortcomings can increase the cost of the sample collectors, interfere with the collection process, and/or invalidate the integrity of samples.

SUMMARY OF THE INVENTION

The present invention is a fluid sampler especially suitable for sampling seawater for research purposes although it can be obviously adapted and/or employed for sampling any liquid or gas. This invention uses a bladder inflated by conventional means with a gas to the pressure corresponding to the hydrostatic pressure or other pressure of the fluid to be sampled. The bladder is enclosed in a pressure tank which has a valved opening to allow fluid flow through its wall. Once the apparatus is immersed in the fluid which is to be sampled, means for slowly exhausting the gas from the bladder, possibly a pump, are activated whereby the hydrostatic or other pressure of the fluid collapses the bladder and the fluid sample quiescently fills between the pressure tank and the bladder through the valved opening. When sample collection is complete, the valved opening, which is locally or remotely controlled, is closed and the sample is retrieved. Residual or ullage gas in the bladder acts as a pressure reservoir and maintains the sample at the pressure at which it was collected. After connecting the sampler to an examining device or collecting tank, bladder inflating means are again employed to initiate sample flow from the pressure tank to the examining device or collecting tank at the same pressure that exists in the sampler.

Accordingly, it is an object of this invention to provide a fluid sampler which can recover fluids containing microorganisms, microbubbles, and particles from great depths in undamaged form and maintain these microorganisms, microbubbles, or particles under ambient and stable conditions.

It is another object of this invention to provide a fluid sampler which is capable of collecting fluid samples at a slow, steady rate of flow that involves no sudden pressure changes velocity gradients that might damage or alter any trapped organisms, bubbles, or particles.

It is another object of this invention to provide a fluid sampler which is capable of retrieving samples having volumes approaching the volume of the sampler so as to minimize cost and size of collector required for a specific volume of collected sample.

Yet another object of this invention is to provide a fluid sampler which is capable of collecting a sample and transferring the sample at in situ collection pressure to other instruments or devices for sample examination.

These and other objects and advantages of the present invention will become more fully apparent from the following detailed description when taken in conjunction with the accompanying drawing wherein:

BRIEF DESCRIPTION OF THE DRAWING

The FIGURE is a front pictorial, partial half sectional view of the present invention.

DETAILED DESCRIPTION OF THE PREFERRED EMBODIMENT

Referring now to the FIGURE, the preferred embodiment of the present invention is there shown. The sampling apparatus includes a rigid container 12 which may be constructed of any suitably rigid, fluid-impervious material such as glass, metal, plastic, or the like, the particular material selected to provide structural integrity, rigidity, corrosion resistance, and ability to withstand any pressure differentials to which the container 12 may be subjected during operation. The rigid container 12 is shown in the FIGURE as being tank-shaped, and may be of any size large enough to contain a scientifically sufficient sample, but otherwise should be small enough to not unduly hamper handling and incur loss. Twenty-five gallons would be a typical capacity volume for microbubble research purposes although the device could be much larger or smaller depending upon the size of sample required for a particular purpose, material used to form the container, and means available for transporting and handling the apparatus. Other shapes, such as spherical, are also possible, the best shapes being those which best accommodate an enclosed bladder 14 having a single bladder opening, said bladder described further below, during all its states of inflation and deflation.

The rigid container 12 has two ports. One port receives the bladder 14 and, in conjunction with the surrounding container wall, accommodates conventional closing means 16, such as a screwable lid, for covering the bladder opening and hermetically sealing the periphery of the bladder opening around the rim of the port. The closing means 16 has two conduits, although only one could be used, through which gaseous communication, in the absence of an obstruction, is established between the outside of the rigid container and the inside of the bladder. The second port in container 12 provides fluid communication between the outside and inside of container 12 in the absence of an obstruction. Hence, fluid flow through the two conduits in the closing means 16 travels between the outside of the container 12 and the inside of the bladder 14; fluid flow through the port in container 12 that does not have closing means 16 travels between the outside of the container 12 and the inside of the container 12.

All ports have valve means for allowing and stopping fluid flow through the ports. Fluid-impervious tubing 17 interconnects port openings and associated valve means with each interconnection point being hermetically sealed. In the embodiment shown in the FIGURE, the first conduit in closing means 16 has a valve means comprising a gaseous inlet valve 18 with an associated pressure gauge 20 for injecting gas into the bladder 14. The second conduit in closing means 16 utilizes a remotely energized solenoid valve 22/check valve 24 combination for allowing gas to leave the bladder 14. A solenoid valve 26/high pressure reservoir 28/valve 30/valve 37/pneumatic actuator 32/spring-loaded ball valve 34 combination controls flow in the second port that communicates flow from outside to inside the rigid container 12. In all cases, other valve powering, actuation, and constituent means may be employed provided that the resultant valve means performs the operations specified above and described more fully below. In some cases, because of the weight of some portions of the valve means and their positioning external to the rigid container, support means for the valve means may be required to hold the valve means in position. In the embodiment in the FIGURE such support means are employed and comprises six metal bars 25 (only three of which are shown) to which individual portions of the valve means are attached by conventional means (not shown), said metal bars being welded together and to the outside of the rigid container and configured as partially shown in the FIGURE. The three bars not shown project from the two fully shown and one partially shown circular cutaways, respectively, and converge at a point approaching the viewer so as to form, with the three bars 25 shown, a triangular base for the sampler with three support bars connecting the corners of the triangle to the container 12. In addition, the support means comprises a removable clamp 29 which supports the check valve 24 by holding it against an apparatus lowering cable 31. Employment of this latter type of support arrangement is especially suitable for use when the apparatus is deployed in its preferred embodiment to sample seawater because it facilitates control over the rate of gaseous discharge through the check valve 24, the reason for the discharge explained further below, by allowing the check valve to be positioned at any number of heights (with associated hydrostatic pressures) above the rest of the apparatus. Cable 31 also has internal electrical wires that connect to solenoid valves 22 and 26. The other ends of the wires are connected to a remote electrical power supply not shown in the FIGURE. Disposed within the rigid container 12 is a bladder 14 formed of rubber or any other suitable elastomer material. For general use, the bladder 14 should conform to the contours of the inside of the rigid container 12 when inflated to collection pressure, to purge the container 12 of ullage from previously collected samples.

As in the preferred embodiment, a screen 36 or similar non-flow-interrupting element may be employed to present a smooth inner surface to an inflated bladder 14. The bladder 14 has a single opening which is hermetically sealed, as described above, around the rim of one of the ports of the rigid container 12.

A metal ring 38 or similar element to which a lowering cable can connect is attached to the device by conventional means.

In the absence of hydrostatic pressure, that is, for embodiments different than the preferred embodiment which is especially suitable for sampling seawater, a pump 40 is shown inserted amid the fluid-impervious tubing 17 interconnecting valves 22 and 24. This pump could be employed to pump gas out of the bladder 14, as required. This embodiment would replace the preferred embodiment in which valves 22 and 24 utilize the hydrostatic pressure differential between valve 24 and bladder 14 to push gas out of the bladder 14.

The preferred embodiment of the present invention, the embodiment shown in the FIGURE with the pump 40 omitted, operates as follows. In preparation for use, the bladder 14 is inflated via the gaseous inlet valve 18 and first conduit in closing means 16 to the pressure corresponding to the in situ pressure at which the water sample will be collected. Also in preparation for use, reservoir 28 is pressurized with gas through valve 30 while valve 37 is opened to the atmosphere. During this time solenoid valve 26 is closed. The gas pressure differential across actuator 32 keeps valve 34 open. Valves 30 and 37 are then closed, and valve 34 remains open. If microbubble spectroscopy work is to be performed, the rigid container 12 should be initially purged with degassed water so that any initial voids are filled with degassed water. Utilizing the cable connecting element 38, the sampler is lowered to the desired depth. At the desired depth, the solenoid valve 22 connected to the inside of the bladder 14 is energized, by an operator switching electrical power to it through the conductors in cable 31 from the remote power supply not shown allowing the hydrostatic pressure differential between the bladder 14 and the check valve 24, which is held above the bladder 14 at a predetermined position depending upon flow rate desired, to collapse the bladder 14 and force the gas within the bladder 14 through the second conduit in closing means 16 and then out. As noted above, this operation, in an alternative embodiment for use in an environment without hydrostatic pressure, could be achieved with a pump 40. As gas leaves the bladder, water flows slowly through the valve 34 into the rigid container 12. This flow continues until the desired volume of sample has been collected. Then valve 22 is deenergized by an operator remotely disconnecting power to it and the filling flow stops. The remaining gas in the bladder 14 acts as a pressure accumulator. The solenoid attached to the valve 26 is energized by an operator who connects power to the solenoid through the wires in cable 31 and it allows the pressure across valve 26 to equalize. With no pressure differential across the actuator 32, an internal spring closes the ball valve 34. The sampler is then retrieved. When the sampler is in place near a device that will examine the water sample, the outlet of valve 34 is connected to wherever the fluid is to go, and any empty volume in that connection is purged with fluid similar to that which has been sampled. Then gas is connected to the gas inlet 18 to the bladder 14 through a pressure regulator. The outlet pressure to valve 18 is adjusted to equal the bladder pressure. With the valve in the examining device closed, pressure is again applied to the high pressure reservoir 28 so as to open the ball valve 34 by means of the resultant pressure differential. Because of water's incompressibility, the entire system is still at bladder pressure. When a controlling valve in the water examining device is then opened, water will pass out of the pressure tank 12 as gas fills the bladder 14 and expands it simultaneously. In a typical case, the flow rate through the valve 34 should not exceed 3 gallons per minute as that is the maximum volume flow rate which most pressure regulators can deliver while maintaining in situ pressure into the bladder 14. Microbiologicals and microbubbles within the water delivered by the sampler 10 to the water examining device will be undamaged, unaltered, and maintained at the ambient conditions from which they were retrieved.

Obviously, numerous modifications and variations of the present invention are possible in light of the above teachings. It is therefore to be understood that within the scope of the appended claims, the present invention may be practiced otherwise than as specifically described hereinabove.

What is claimed is:

1. A fluid sampler for acquiring fluid samples at in situ conditions comprising:
    a rigid container having first and second openings in the wall thereof for containment of volumes of sample approximately equal to to the volume of said rigid container;
    a bladder to act as a pressure reservoir having a single bladder opening disposed within said rigid container;
    closing means for covering the bladder opening and hermetically sealing the periphery of the bladder opening around the rim of the first opening in the wall of the rigid container, said closing means having two conduits, a first conduit and a second conduit, therethrough through which fluid communication is established between the outside of the rigid container and the inside of the bladder in the absence of an obstruction;
    first valve means for controlling fluid flow through the first conduit from outside the rigid container and closing means to inside the bladder;
    means for controlling fluid flow through the second conduit from inside the bladder to outside the rigid container and closing means;
    second valve means for controlling fluid flow through the second opening in the wall of said rigid container;
    fluid-impervious tubing interconnecting the first conduit through said closing means and said first valve means for controlling fluid flow, said fluid-impervious tubing being hermetically sealed at each interconnecting point;
    additional fluid-impervious tubing interconnecting the second conduit through said closing means and said means for controlling fluid flow through the second conduit, said fluid-impervious tubing being hermetically sealed at each interconnecting point;
    additional fluid-impervious tubing interconnecting the second opening in the wall of said rigid container and said second valve means, said fluid-impervious tubing being hermetically sealed at each interconnecting point;
    support means for holding the first valve means, means for controlling fluid flow through the second conduit and second valve means in predetermined positions around said rigid container;
    means for remotely controlling said means for controlling fluid flow; and
    means for remotely controlling said second valve means.

2. The fluid sampler of claim 1 wherein:
    said means for controlling fluid flow through the second conduit from inside the bladder to outside the rigid container further comprises pumping means.

* * * * *